United States Patent [19]

Cullis

[11] 4,093,545
[45] June 6, 1978

[54] METHOD AND APPARATUS FOR DETERMINING THE AMOUNT OF ULTRAFILTRATION DURING DIALYSIS

[75] Inventor: Herbert M. Cullis, Silver Spring, Md.

[73] Assignee: Baxter Travenol Laboratories, Inc., Deerfield, Ill.

[21] Appl. No.: 550,051

[22] Filed: Feb. 14, 1975

[51] Int. Cl.² ............................................. B01D 31/00
[52] U.S. Cl. ..................................... 210/86; 210/136; 210/321 B
[58] Field of Search ...................... 210/87, 88, 22, 321, 210/86, 136; 137/99; 417/397, 404

[56] References Cited

U.S. PATENT DOCUMENTS

| | | | |
|---|---|---|---|
| 3,416,664 | 12/1968 | Kumme et al. | 210/321 X |
| 3,669,880 | 6/1972 | Marantz et al. | 210/321 X |
| 3,844,940 | 10/1974 | Kopf et al. | 210/88 X |
| 4,021,341 | 5/1977 | Cosentino et al. | 210/87 |

Primary Examiner—Frank A. Spear, Jr.
Attorney, Agent, or Firm—Henry W. Collins; Garrettson Ellis; Richard G. Kinney

[57] ABSTRACT

A dialysis device is disclosed which includes dialysis solution conduit means for passing dialysis solution through a membrane dialyzer. In accordance with this invention, controlled volumes of dialysis solution are supplied and withdrawn to and from at least a portion of the dialysis solution conduit means, plus the dialyzer connected to the conduit means. By this, the input and output of the dialysis solution to and from the conduit portion and connected dialyzer is positively controlled. The total liquid volume of the conduit portion and connected dialyzer is measured. Accordingly, changes in the total liquid volume which are not attributable to the dialysis solution input and output indicate the amount of ultrafiltration during dialysis.

5 Claims, 1 Drawing Figure

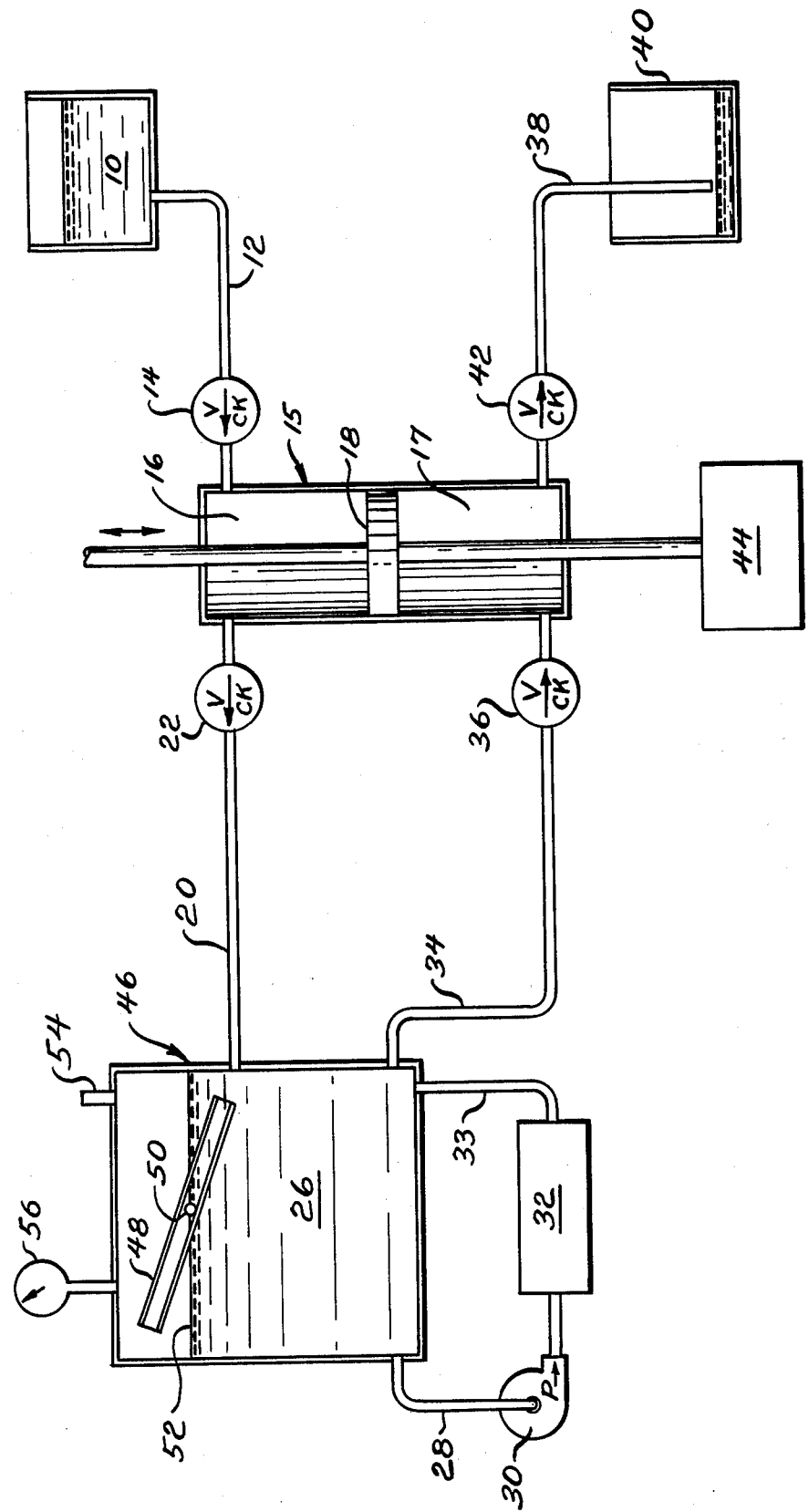

METHOD AND APPARATUS FOR DETERMINING THE AMOUNT OF ULTRAFILTRATION DURING DIALYSIS

BACKGROUND OF THE INVENTION

Dialysis apparatus is used as an artificial kidney for dialyzing blood, as well as for many other purposes such as purification of various chemical or biological products, and the like.

Solutes in the various solutions which are brought into contact with a dialysis membrane pass through the membrane at a rate which is related to the difference in the concentration of such solutes, at opposite sides of the membrane. However, water tends to pass through dialysis membranes in a manner which is more dependent upon the transmembrane pressure, and is less dependent upon concentration. Accordingly, during blood dialysis, for example, the amount of water which passes from the blood of the patient across the dialysis membrane (which phenomenon is known as "ultrafiltration") is dependent upon the overall transmembrane pressure, which in turn is dependent upon the pressure drop in the blood and dialysis solution flow paths of the dialyzer, and other pressure factors.

The amount of ultrafiltration from the blood which takes place is, of course, a critical medical factor in the treatment of a uremic patient. Physicians who perform dialysis upon their patients generally desire that a specific, pre-determined amount of ultra-filtration take place during each dialysis operation. Conventionally, the patient may be weighed, and his weight loss calculated in order to determine the amount of ultrafiltration which has taken place. However, this rather cumbersome method does not account for other factors which may cause the weight to vary, such as eating or elimination during the four to six hour course of blood dialysis, and loss of weight through perspiration and the like.

Accordingly, there is a need for a technique for directly measuring the amount of ultrafiltration, while at the same time permitting a large amount of dialysis solution to pass through the dialyzer, for example by means of the very popular "single pass" mode of dialysis, in which the dialysis solution passes only once through a stacked plate type or fiber type dialyzer and then is discarded. The same need exists in the "recirculating-single pass" technique of dialysis in which large volumes of dialysis solution are passed through a coil type dialyzer in a semi-recirculating mode, with dialysis solution being continuously added and withdrawn from the system.

The REDY dialysis system, which is commercially available at the present time, can utilize the direct measurement of ultrafiltration by measuring any increase in the total volume of dialysis solution used. This, however, is possible only because a relatively small amount of dialysis solution, measuring only a few liters, is used. The dialysis solution is continuously recirculated through the dialyzer, being continuously purified. This technique has not been chosen by the majority of doctors, who appear to prefer the use of a large volume of dialysis solution, which precludes the accurate measurement of total volume of dialysis solution as a means for measuring the amount of ultrafiltration.

In accordance with this invention, a system is provided which permits the direct measurement of ultrafiltration in a system in which dialysis solution may be added and withdrawn on a continuous basis, or on any other basis as desired. Accordingly, the currently preferred medical dialysis techniques can be performed, while at the same time one can directly determine the total amount of ultrafiltration which has taken place at the time during the dialysis operation. Accordingly, the physician can adjust the conditions of the dialysis operation to increase or decrease the rate of ultrafiltration as his judgment would indicate.

DESCRIPTION OF THE INVENTION

In accordance with this invention, a dialysis system is provided which includes dialysis solution conduit means for passing dialysis solution through a membrane dialyzer.

In accordance with this invention, means are provided for supplying and withdrawing controlled volumes of dialysis solution to and from at least a portion of the dialysis solution conduit means and a dialyzer connected to the conduit means, to positively control the input and output of dialysis solution to and from the conduit portion and connected dialyzer. Means are also provided for measuring the total liquid volume of the conduit portion and connected dialyzer. Accordingly, changes in the aforesaid total liquid volume which are not attributable to the dialysis solution input and output indicate the amount of ultrafiltration during dialysis.

It is generally preferable for the volume of dialysis solution supplied and the volume withdrawn from the conduit portion and connected dialyzer to be identical, so that the liquid volume attributable to dialysis solution in the conduit portion and connected dialyzer remains constant. Accordingly, any increase or decrease in such liquid volume is a direct measurement of ultrafiltration in one direction or the other across the dialysis membrane of the dialysis device. This is accomplished in the specific embodiment shown in the drawing by means of a double-faced piston in a manner to be described below, but any means for supplying and withdrawing controlled volumes of dialysis solution can be used in accordance with this invention, e.g., a positive displacement volumetric pump such as another type of piston pump, a gear pump, a peristaltic pump; or any other pump which is coupled to a flow measuring device such as a Rotometer flow measuring device, a Doppler effect fluid flow meter, or any other fluid flow meter which can accurately measure and accordingly permit control of the volume of fluid pumped. Separate pumps can be used for the inflow and outflow of dialysis solution to the controlled volume area defined by the conduit portion and dialyzer described above, or a single pump means can serve both the dialysis solution inlet and outlet.

Other means for supplying and withdrawing controlled volumes of dialysis solution may include a centrifugal pump which incorporates a volume compensating metering valve, or any other volume compensated pump. The means for supplying and withdrawing controlled volumes of dialysis solution may be a single pump operated in a simultaneous mode such as the double faced piston pumps specifically disclosed herein, or in a time-shared mode, where a single pump supplies and withdraws dialysis solution in an alternating phased manner.

The means for measuring the total liquid volume of the conduit portion generally comprises a vented dialysis solution storage chamber where variable volumes of dialysis solution may be stored, plus means for measuring the amount of dialysis solution in the storage chamber. The storage chamber can be a simple burette member connected to the remainder of the dialysis solution conduit means in any conventional manner, so that the conduit means portion and connected dialyzer which are kept in a controlled volume condition by the supplying and withdrawing means are completely filled with dialysis solution, and any varying volume of dialysis solution is retained in the burette. Accordingly, the dialysis solution level in the burette means can be visually measured by calibrated volume markers on the burette means.

The means for measuring the total liquid volume specified above can also comprise a container of known volume similar to that described above, but in which the volume of solution contained therein is measured by other means such as electronic level, volume, or pressure senser means operating on resistance capacitive, indicative, photoelectric or piezoelectric principles.

All other things being equal, it is generally preferable to avoid electronic measuring components and the like to accomplish the purposes of this invention, in order to avoid the possibility of damage to blood cells or the like by electrical shock, through an accidental short circuit. The embodiment below discloses a relatively simple, safe, mechanical means for accomplishing the purposes of this invention.

The apparatus of this invention should also be either readily sterilizable or disposable in order to avoid the danger of transmission of an infectious disease such as hepatitis through leaks of the patient's blood into the dialysis system.

The above-described advantages are achieved in a particularly effective way by the specific embodiment of this invention, described in the drawing below, which is a diagrammatic representation of a dialysis system of this invention.

Referring to the drawing, a dialysis system is shown having a dialysis solution supply source 10, from which a supply conduit 12 leads through one-way valve 14 into chamber 15, which contains reciprocating, double-faced piston 18, which divides chamber 15 into a pair of variable volume chamber sections 16, 17. One-way valve 14 is positioned to prevent dialysis solution from passing once again out of chamber 15 and into supply conduit 12. Second supply conduit 20 communicates at one end with chamber 16, and at its other end with dialysis solution storage chamber or container 26, which, as previously stated, may be simply a burette connected to conduit 20, and at an elevated level, so that dialysis solution in the burette member will be supplied to the entire system, and any variability of volume of dialysis solution in the system is indicated by the liquid level in the burette member. Supply conduit 20 passes through one-way valve 22, to prevent dialysis solution in supply conduit 20 from flowing back into chamber 16.

In the specific embodiment of this invention, dialysis solution chamber 26 is a tank with which supply conduit 20 communicates. While any desired system may be used for conveying dialysis solution from chamber 26 to the actual membrane dialyzer, the system shown herein includes conduit 28, which leads to pump 30, which may be a centrifugal pump or other suitable device. Pump 30 in turn communicates with a membrane dialyzer unit 32, and from there dialysis solution may be returned to chamber 26 by conduit 33. Dialyzer 32 may in this particular instance comprise a stacked plate dialyzer such as a kiil type dialyzer.

Alternatively, dialyzer 32 may be a coil dialysis system such as an RSP ® Dialyzer unit, sold by Travenol Laboratories, Inc., of Morton Grove, Illinois.

Dialysis solution then may be conveyed by conduit 34 from chamber 26, across one-way valve 36 to chamber section 17, on the other side of piston 18 from chamber section 16.

Dialyzer 32 and pump 30 may also be directly positioned on conduit 34 to avoid the recirculation of dialysis solution to chamber 26 as shown in the drawing. However, in this case it is desirable to operate piston 18 and cylinder 15 so that it pumps at a faster rate than any pump in line 34. Should piston 18 cease to operate, the pump in line 34 would continue to pump dialysis solution across variable volume chamber 17 and out of the system, resulting in a possible change in the volume of dialysis solution in controlled volume area 46. This in turn could interfere with the determination of the amount of ultrafiltration which has taken place.

Outlet conduit 38 leads from chamber section 17 to a discard location 40 for the spent dialysis solution. One-way valve 42 is positioned in conduit 38 to prevent dialysis solution from passing back from conduit 38 into chamber section 17, while one-way valve 36 prevents dialysis solution from passing from chamber section 17 back to chamber 26.

The one-way valves utilized herein may conveniently be spring loaded ball valves, although duck billed valves are also suitable, as are swinging check valves, slide valves, rotating valves, or the like.

As a result of this structure, as piston 18 reciprocates by the action of reciprocating motor 44 back and forth in chamber 15, to increase and decrease the respective volumes of chamber section 16 and 17 in an alternating manner, dialysis solution is pumped from source 10 through conduits 12 and 20 into chamber 26. Correspondingly, dialysis solution is pumped through conduits 34 and 38 in exactly the same volume as the dialysis solution which is introduced to chamber 26, through the action of piston 18 in cylinder 15.

As a result, the amount of dialysis solution which is found at any given time during operation in controlled volume area 46 (which includes all of conduit 20 to the left of one-way valve 22, chamber 26, pump 30, dialyzer 32 and its adjacent conduits, plus all of conduit 34 to the left of one-way valve 36) remains unchanging, as long as no air is passed into conduit 20 or out of conduit 34. This constant relationship will exist irrespective of the rate of operation of piston 18 or the length of its stroke. Similarly, factors such as temperature, pressure and osmolality of the dialysis solution and the like have little varying effect on the volume of dialysis solution in controlled volume area 46, in normal usage.

Liquid level measuring tube 48 is positioned in chamber 46 in angular relation to the horizontal. Float ball 50 is positioned in tube 48, so that it rises and falls with the liquid level in chamber 26, moving substantially more to the left or right than up or down during such rising and falling, due to the orientation of tube 48. A suitable stop member is positioned at each end of tube 48 to prevent ball 50 from falling, but also permitting liquid to pass into the interior of tube 48 for flotation of ball 50.

Tube 48 may then be appropriately marked so that the volume of solution in container 26 can be measured by the simple reading of the position of ball 50 against a volume indicating scale marked on tube 48. Accordingly, at the beginning of dialysis, after the device of this invention has been primed by inserting dialysis solution and removing all air from controlled volume system 46 except in the area of container 26 above liquid level 52, the liquid level 52 is noted by means of scaled tube 48 and float ball 50, and recorded. During dialysis, ultrafiltration takes place from the blood of the patient, which causes a net increase in the liquid volume in controlled area 46 which corresponds to the amount of ultrafiltration which has taken place, because piston 18 and cylinder 15 necessarily supply and remove essentially identical amounts of dialysis solution from controlled volume area 46. Accordingly, at any time during the course of dialysis, the liquid level 52 can be determined by taking a reading of tube 48. Any increase in the liquid level is attributable to ultrafiltration which has taken place, and, in this embodiment, the exact volume of ultrafiltration which has taken place can be directly read from tube 48.

Vent 54 permits liquid level 52 to rise and fall without changes in pressure in container 26. However, vent 54 may be sealed, if it is desired to automatically limit the amount of ultrafiltration which can take place during the dialysis operation. As the liquid level 52 rises in container 26 due to ultrafiltration, the pressure in the container increases if vent 54 is sealed. This increase in pressure is of course transmitted into the dialysis solution flow path of the dialyzer, where it tends to partially counterbalance the overpressure which is generally present at the dialysis membrane on the blood side. Since ultrafiltration is a pressure-related phenomenon, this counterbalancing of the overpressure on the blood side of the membrane tends to reduce the ultrafiltration automatically, with the reduction of such ultrafiltration increasing as the pressure in container 26 increases.

Cylinder 15 is typically made of stainless steel, and piston 18 may be made of a material having good sealing properties such as polytetrafluoroethylene (Teflon).

Pressure gauge 54 indicates any pressure build-up in container 26 when vent 54 is sealed. Piston 18 and cylinder 15 may, if desired, be replaced by an appropriate sliding valve arrangement working in conjunction with a piston and cylinder, being controlled by rotating cams or the like, so that the piston and cylinder supplies and withdraws controlled amounts of dialysis solution and preferably identical amounts thereof. It is contemplated that the amount of dialysis solution supplied to controlled volume area 46 could be different from the amount withdrawn, as long as the difference is known, so that the change in liquid level 52 over a period of time in the absence of any ultrafiltration can be predicted. Accordingly, any deviations from that changing liquid level will indicate the amount of ultrafiltration which has taken place.

The above has been offered for illustrative purposes only, and is not intended to limit the scope of this invention, which is as defined in the claims below.

That which is claimed is:

1. In a dialysis system which includes dialysis solution conduit means for passing dialysis solution through a membrane dialyzer, the improvement comprising:

means for supplying and means for withdrawing essentially identical volumes of dialysis solution to and from a portion of said dialysis solution conduit means and a dialyzer connected to said conduit means, to precisely and positively control the input and output of dialysis solution to and from said conduit portion and connected dialyzer;

container means capable of holding a variable liquid volume and connected to said portion of the dialysis solution conduit means which is under precise positive control of the input and output of dialysis solution; and means for measuring the total liquid volume of dialysis solution in said precisely, positively controlled conduit portion and connected dialyzer, said total liquid volume being less than the entire liquid volume of dialysis solution in said dialysis system, whereby changes in said total liquid volume indicate the amount of ultrafiltration during dialysis; in which said means for supplying and means for withdrawing identical liquid volumes comprises double-faced piston means, reciprocable in a chamber, and defining a first, variable volume chamber portion adjacent one face of said piston, and a second, variable volume chamber portion adjacent the opposite face of said piston; a dialysis solution supply conduit, as part of said dialysis solution conduit means, communicating with said first chamber portion; first one-way valve means in said supply conduit for causing dialysis solution to be supplied to said first chamber as said piston causes its volume to expand, and to be expelled into said conduit portion and connected dialyzer as said piston causes said volume to contract, said second chamber portion communicating with a dialysis solution withdrawing conduit as part of said dialysis solution conduit means, and second one-way valve means for permitting dialysis solution to be withdrawn from said conduit portion and connected dialyzer into the second chamber as said piston causes the volume of said second chamber to expand, and for permitting dialysis solution to be expelled from said second chamber and from the dialysis system as the volume of said second chamber contracts, through reciprocating motion of said piston.

2. The dialysis device of claim 1 in which said means for measuring the total liquid volume comprises liquid level measuring means positioned in said container means.

3. The dialysis device of claim 2 in which said container means is sealed from the exterior.

4. The dialysis device of claim 2 in which said container means is vented to the exterior.

5. The dialysis device of claim 1 in which said conduit portion and connected dialyzer in which the liquid volume is controlled includes a supply conduit leading between the double-faced piston means and the container means for transferring dialysis solution from the piston means to the container means; a solution withdrawing conduit leading between the container means and the double-faced piston means for withdrawing dialysis solution from said container means; dialyzer conduit means having both an inlet and an outlet communicating with said container means and adapted to communicate with the inlet and outlet of said dialyzer, and pump means positioned in communication with said dialyzer conduit means to cause dialysis solution to flow from said container means through the dialyzer conduit, through said dialyzer, and back to said container means.

* * * * *